United States Patent [19]

Fujino et al.

[11] Patent Number: 4,559,324

[45] Date of Patent: Dec. 17, 1985

[54] POLYPEPTIDE-DIESTERS, THEIR PRODUCTION AND USE

[75] Inventors: Masahiko Fujino, Hyogo; Chieko Kitada, Osaka, both of Japan

[73] Assignee: Takeda Chemical Industries, Ltd., Osaka, Japan

[21] Appl. No.: 513,340

[22] Filed: Jul. 13, 1983

[30] Foreign Application Priority Data

Jul. 28, 1982 [JP] Japan .................................. 57-132657

[51] Int. Cl.$^4$ ...................... C07C 103/52; A61K 37/02
[52] U.S. Cl. ........................................ 514/14; 514/15; 514/16; 514/17; 260/112.5 R
[58] Field of Search .................. 260/112.5 R; 424/177

[56] References Cited

U.S. PATENT DOCUMENTS 4,218,474 8/1980 Barnish et al. ...................... 424/177

*Primary Examiner*—Delbert R. Phillips
*Assistant Examiner*—F. T. Moezie
*Attorney, Agent, or Firm*—Wegner & Bretschneider

[57] ABSTRACT

Novel polypeptide-diesters, inclusive of salts thereof, which have the formula:

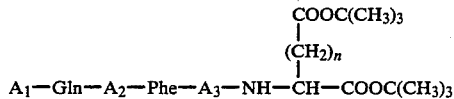

wherein $A_1$ is arginine or lysine or a di- or tripeptide residue having arginine or lysine at its N-terminal; $A_2$ is an aromatic amino acid residue; $A_3$ is a neutral amino acid or aromatic amino acid residue; each of the amino acid residues mentioned may be optionally L-configured or D-configured; and n is 0, 1 or 2. These compounds are useful as analgesics.

14 Claims, No Drawings

POLYPEPTIDE-DIESTERS, THEIR PRODUCTION AND USE

This invention relates to new polypeptide-diesters, a method for production of the same and an analgesic containing any one of the compounds.

More particularly, the invention relates to an antagonistic drug against Substance P which is a neurotransmitter.

Since M. M. Chang et al [Nature New Biology, 232, 86 (1971)] identified the chemical structure of substance P as

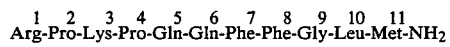
$$\overset{1}{\text{Arg}}-\overset{2}{\text{Pro}}-\overset{3}{\text{Lys}}-\overset{4}{\text{Pro}}-\overset{5}{\text{Gln}}-\overset{6}{\text{Gln}}-\overset{7}{\text{Phe}}-\overset{8}{\text{Phe}}-\overset{9}{\text{Gly}}-\overset{10}{\text{Leu}}-\overset{11}{\text{Met}}-NH_2$$

and considered the substance to be a transmitter of pain, a number of its analogs have been synthesized for developing antagonists against substance P and their antagonist activities investigated. To this day, however, only two compounds, namely (D-Pro$^2$, D-Phe$^7$, D-Trp$^9$)-Substance P and (D-Pro$^2$, D-Trp$^7$, D-Trp$^9$)-Substance P, are known to be sufficiently active [S. Rosell and K. Folkers, TIPS, 211 (1982)]. Both of these compounds are comparatively large peptides consisting of 11 amino acid residues like Substance P and are not easy to synthesize chemically and, therefore, it is difficult to provide either of them in quantities warranting clinical use. Moreover, in order that these compounds may penetrate into the brain and spine to display their analgetic and other pharmacologic actions, they have to be administered directly to these sites and this factor alone is sufficient to make their clinical application difficult.

The present inventors conducted a series of researches to develop a compound which would be economically advantageous, stable as a chemical compound and sufficiently effective, in terms of analgetic and other pharmacologic effects, even when administered intravenously, subcutaneously or intralumbally, and discovered that a specific compound having a di-tertiary butyl ester of an acidic amino acid at the C-terminal end meets the above-mentioned requirements. The finding was followed by further investigations which have resulted in the discovery of an effective peptide containing 6 to 8 amino acid residues. The present invention is based on the above discovery.

(1) a polypeptide-diester of the formula (I):

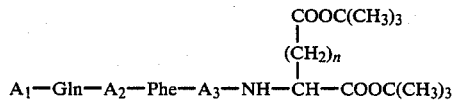

wherein $A_1$ is arginine or lysine or a di- or tripeptide residue having arginine or lysine at its N-terminal; $A_2$ is an aromatic amino acid residue; $A_3$ is a neutral amino acid or aromatic amino acid residue; each of the amino acid residues mentioned may be optionally L-configured or D-configured; and n is 0, 1 or 2, or a pharmaceutically acceptable salt thereof, (2) a method of producing a polypeptide-diester of the formula (I), which comprises condensing either arginine or lysine or a partial peptide having arginine or lysine at its N-terminal end and other amino acid unit or units in the above amino acid sequence with a partial peptide ester or amino acid ester corresponding to the remainder of the above desired polypeptide by a peptide synthesizing technique.

(3) An analgesic containing a polypeptide-diester of formula (I) or a pharmacologically acceptable salt thereof.

Throughout this specification, the amino acids, peptides, protective groups, condensing agents, etc. are indicated by the abbreviations according to the IUPAC-IUB (Commission on Biological Nomenclature) which are in common use in the field of art. Moreover, unless otherwise stated, the amino acids and their residues when shown by such abbreviations are meant to be L-configured compounds and residues, while the D-compounds and residues are shown with the prescript of [D-].

Referring to the polypeptide derivative of formula (I), the peptide residues or amino acid residues as designated by $A_1$, $A_2$ and $A_3$ are exemplified as follows.

The amino acid or acids constituting the di- or tripeptide residue having either arginine or lysine at its N-terminal, as represented by $A_1$, are generally preferably neutral amino acids such as glycine, D- or L-proline, D- or L-threonine, D- or L-serine, D- or L-alanine, D- or L-valine, D- or L-leucine, D- or L-isoleucine, D- or L-glutamine, D- or L-asparagine, etc.

The aromatic amino acid $A_2$ may for example be D- or L-tryptophan, D- or L-phenylalanine, D- or L-tyrosine or the like.

The neutral amino acid $A_3$ is exemplified by glycine, D- or L-alanine, D- or L-valine, D- or L-leucine, D- or L-isoleucine, etc. and the aromatic amino acid $A_3$ is exemplified by D- or L-tryptophen, D- or L-tyrosine, D- or L-phenylalanine, etc.

The polypeptide-diesters (I) of the present invention are produced by condensing an amino acid or partial peptide as a component of the desired polypeptide-diester with the remainder of the same polypeptide derivative by a peptide-synthesizing technique. This peptide-synthesizing technique may be a known one. Thus, there may be mentioned the azide method, chloride method, acid anhydride method, mixed acid anhydride method, DCC method, active ester method, Woodward's reagent K method, carbodiimidazole method, oxidation-reduction method, DCC/additive method, etc. The N-carboxyanhydride (NCA) method may also be employed when suitable.

Before carrying out this condensation reaction, the carboxyl or/and amino groups of the starting materials which will not be involved in the condensation reaction may be adequately protected or/and the carboxyl or/and amino groups which will be involved in the reaction may be adequately activated.

For example, the amino-protecting group for the arginine or lysine of $A_1$ is preferably a group that can be removed by catalytic reduction, such as benzyloxycarbonyl, chloro- or nitro-substituted benzyloxycarbonyl, etc. Moreover, as the group for protecting the guanidino group of arginine, nitro group is also useful, besides the above-mentioned protective groups. In the case of arginine, it is also desirable to form a salt with a strong acid. As to the amino-protecting groups for starting compounds other than $A_1$, there may be employed benzyloxycarbonyl, t-butoxycarbonyl, isobornyloxycarbonyl, nitrophenylthio and so on.

As for the carboxyl-protecting groups, there may be employed alkyl esters, benzyl esters, t-butyl esters, etc. and salts with sodium, potassium, lithium or t-alkylamines are also useful. The activated forms of carboxyl groups in starting materials include, among others, the corresponding acid anhydrides, azides, active esters (e.g. esters with p-nitrophenyl, pentachlorophenyl, 2,4,5-trichlorophenyl, 2,4-dinitrophenyl, etc. and esters with N-hydroxisuccinimide, N-hydroxyphthalimide, N-hydroxybenzotriazole, N-hydroxy-5-norbornene-2,3-dicarboximide, etc.), and so on.

The condensation reaction according to this invention (peptide forming reaction) can be conducted in the presence of a solvent. The solvent may be selected from among the solvents known to be useful for peptide synthesis. For example, anhydrous or aqueous dimethylformamide, dimethyl sulfoxide, pyridine, chloroform, dioxane, dichloromethane, tetrahydrofuran, ethyl acetate, ether, etc. as well as suitable mixtures thereof may be mentioned.

The reaction temperature is generally selected within the range of about $-20°$ C. to about $50°$ C. The intermediate protected peptides which are used as precursors of compounds of the present invention can be easily produced by the conventional technique of solid phase synthesis.

When the resulting condensation product has protective groups, it is subjected to deprotection reaction. While the kind of this reaction depends on the protective groups employed, it is commercially advantageous to see to it that all the protective groups present are removed in a sigle operation without affecting the peptide bonds and the t-butyl ester bonds at the C-terminal of the polypeptide. Accordingly, the protective groups are selected in consideration of this factor. The most useful method for deprotection is catalytic reduction in the presence of a catalyst such as palladium black, palladium-on-carbon, platinum, etc. The deprotection reaction is conducted at room temperature, and generally an alcohol, acetic acid or water is used as the solvent.

After completion of the reaction, the product polypeptide-diester (I) is isolated by the conventional peptide recovery procedure such as extraction, distribution, reprecipitation, recrystallization, column chromatography, etc. The polypeptide-diester (I) can be obtained in the form of a salt by treating it with an organic or inorganic acid in the per se known manner and generally speaking, the acid is preferably acetic acid, citric acid, tartaric acid, hydrochloric acid, or sulfuric acid, for instance.

When tested by the pharmacological test method of Otsuka et al. [M. Otsuka, M. Yanagisawa: J. Exp. Biol. 89, 201 (1980)], the polypeptide-diester (I) according to the present invention causes a marked inhibition of the Substance P-induced depolarization of the spinal cord isolated from a newborn rat at the concentration level of 1 to 100 $\mu$M. Therefore, the compound (I) according to the present invention is a Substance P-antagonist.

The polypeptide-diester (I) of the present invention was further tested in rats by the hot plate method described by G. Weelfe and A. D. Macdonald [Journal of Pharmacology and Experimental Therapeutics 80, 300 (1944)]. As a result, the compound (I) administered intralumbally caused a definite analgetic effect at the dose level of about 0.1 to 200 $\mu$g/rat, which is comparable to the effective dose of morphine. Moreover, this effect is not antagonized by naloxone. Since the analgetic action of the polypeptide-diester (I) is thus non-narcotic, the compound is useful as an analgesic agent.

This polypeptide does not elicit any side effect even when administered at the level of about 10 times its effective dose, i.e. 100 mg/kg.

As a representative example of use, the polypeptide-diester (I) according to the present invention and its pharmaceutically acceptable salt can be advantageously employed for the management of intense pain at the terminal stage of cancer or other general pain conditions in mammalian animals (e.g. mouse, rat, rabbit, dog, monkey, man, etc.).

Generally, the polypeptide-diester (I) of the present invention may be administered in the form of a salt. The recommended dosage for the acetate is generally about 0.001 mg to 10 mg per kg body weight. This derivative is mainly administered parenterally (e.g. intravenous or subcutaneous injection, rectal administration, nasal administration), although it may be orally administered (e.g. tablets, powders, capsules). Continuous infusion or drip infusion at surgery is also useful.

Since this polypeptide derivative is a stable substance, it can be stored as dissolved in physiological saline. For example, it is desirable to employ a saline solution containing about 1 to 20 mg/ml of the salt of compound (I).

The following examples are intended to illustrate the present invention in further detail. In these examples, there are employed the following abbreviations in addition to the abbreviations adopted by the IUPAC-IUB.

HONB: N-hydroxy-5-norbornene-2,3-dicarbodiimide
HOBt: N-hydroxybenzotriazole
DCC: dicyclohexylcarbodiimide
DMF: N,N-dimethylformamide
HPLC: high performance liquid chromatography
—ONB: N-hydroxy-5-norbornene-2,3-dicarbodiimide ester

EXAMPLE 1

Synthesis of H-Arg-Gly-Gln-Phe-Phe-Gly-Asp(OBu$^t$)$_2$:
Z-Phe-Phe-Gly-OH

In 300 ml of methanol was dissolved 5 g of Z-Phe-Gly-OH and catalytic reduction was carried out in a hydrogen gas stream using palladium black as catalyst. The solvent was distilled off, and the residue and 1.96 ml of triethylamine are dissolved in 200 ml of DMF containing 10% of water, followed by addition of 7.74 g of Z-Phe-ONB. The mixture was stirred vigorously for 16 hours. The insoluble matter was filtered off and the solvent was distilled off. To the residue was added water and the resulting crystalline precipitate was collected by filtration, dried and recrystallized from ethanol to give 3.9 g of the above-identified compound.

Yield 55.3%, m.p. 189°–190° C.
$[\alpha]_D^{26} -39.4°$ C. (c=0.36, methanol)
Elemental analysis: Calcd. for $C_{28}H_{29}O_6N_3$: C 66.78; H 5.81; N 8.35, Found: C 66.89; H 6.01; N 8.20.

Z-Phe-Phe-Gly-Asp(OBu$^t$)$_2$

Z-Asp(OBu$^t$)$_2$ (910 mg) was dissolved in methanol and reduced with hydrogen in the presence of palladium black as catalyst. The solvent was then distilled off. The residue, 1.01 g of Z-Phe-Phe-Gly-OH and 720 mg of HONB were dissolved in a mixture of 50 ml of DMF and 20 ml of ethyl acetate, and the solution was ice-cooled. With ice-cooling, 620 mg of DCC was added and the mixture was stirred. After 4 hours of stirring, the temperature was returned to room temperature and the mixture was further stirred for 12 hours. The insoluble matter was filtered off and the solvent was distilled off. To the residue was added water to give a precipitate, which was collected by filtration, dried and recrystallized from methanol.

Yield 925 mg (63.3%), m.p. 178°–180° C. (decompn.)
[α]$_D^{24}$ −17.3° (c=0.54, DMF)
Elemental analysis: Calcd. for C$_{40}$H$_{50}$O$_9$N$_4$: C 65.73; H 6.90; N 7.67, Found: C 65.53; H 6.80; N 7.70.

Z-Gln-Phe-Phe-GLy-Asp(OBu$^t$)$_2$

Z-Phe-Phe-Gly-Asp(OBu$^t$)$_2$ (512 mg) was dissolved in 80 ml of methanol and reduced with hydrogen in the presence of palladium black as catalyst. The solvent was then distilled off. The residue, 235 mg of Z-Gln-OH and 227 mg of HONB were dissolved in 50 ml of DMF and the solution was stirred. With ice-cooling, 191 mg of DCC was added, and the mixture was stirred at 0° C. for 8 hours and at room temperature for 12 hours. The insoluble matter was filtered off and the solvent was distilled off. To the residue was added ethyl acetate and the precipitate was collected by filtration, dried and recrystallized from methanol.

Yield 373 mg (62.2%), m.p. 205°–207° C. (decompn.)
[α]$_D^{24}$ −29.3° (c=0.33, DMF).
Elemental analysis: Calcd. for C$_{45}$H$_{58}$O$_{11}$N$_6$ C 62.92; H 6.81; N 9.78, Found: C 62.85; H 6.92; N 9.90.

Z-Arg(NO$_2$)-Gly-OH

In 10 ml of ethanol was dissolved 2.2 g of Z-Arg(NO$_2$)-Gly-OEt, and 10 ml of 1N NaOH was added dropwise thereto with ice-cooling. The mixture was stirred at 0° C. for 2 hours and neutralized with 10 ml of 1N HCl. The ethanol was then distilled off and the crystalline precipitate was collected by filtration, dried and recrystallized from ethanol-water.

Yield 1.85 g (90.0%), m.p. 123° C. (decompn.)
[α]$_D^{23}$ −8.9° (c=1.0, methanol).
Elemental analysis: Calcd. for C$_{16}$H$_{22}$O$_7$N$_6$: C 46.83; H 5.40; N 20.48, Found: C 46.67; H 5.50; N 20.48.

Z-Arg(NO$_2$)-Gly-Gln-Phe-Phe-Gly-Asp(OBu$^t$)$_2$

Z-Gln-Phe-Phe-Gly-Asp(OBu$^t$)$_2$ (200 mg) was dissolved in 100 ml of DMF and catalytic reduction was carried out in the presence of palladium black as catalyst. The solvent was concentrated to one-third its original volume. To this concentrate were added 115 mg of Z-Arg(NO$_2$)-Gly-OH and 100 mg of HONB and the resulting solution was ice-cooled. To this solution was added 69 mg of DCC and the mixture was stirred at 0° C. for 8 hours and at room temperature for 30 hours. The insoluble matter was filtered off and, then, the solvent was distilled off. To the residue was added acetonitrile and the precipitate was collected by filtration and dried.

Yield 164 mg (63.1%), m.p. 190°–195° C. (decompn.)
[α]$_D^{24}$ −21.3° (c=0.20, DMF).
Elemental analysis: Calcd. for C$_{53}$H$_{72}$O$_{15}$N$_{12}$: C 56.98; H 6.50; N 15.05, Found: C 56.80; H 6.62; N 15.11.

Synthesis of H-Arg-Gly-Gln-Phe-Phe-Gly-Asp(OBu$^t$)$_2$

In 50 ml of acetic acid was dissolved 60 mg of Z-Arg(NO$_2$)-Gly-Gln-Phe-Phe-Gly-Asp(OBu$^t$)$_2$ and catalytic reduction was carried out in a hydrogen gas stream using palladium black as catalyst. The reduction product was lyophilized and dissolved in 0.5 ml of 5N acetic acid. The solution was chromatographed on a Sephadex LH-20 column using the same solvent. The fractions from 107 to 121 ml were combined, lyophilized and purified by HPLC using acetonitrile-water-trifluoroacetic acid (350:650:1) as the solvent to give the above-identified compound.

Yield 20 mg (39.5%),
[α]$_D^{24}$ −16.0° (c=0.15, 3N-acetic acid),
Amino acid analysis: Arg 1.0(1), Asp 1.03(1), Glu 1.07(1), Gly 2.0(2), Phe 1.88(2), (Average recovery 60.4%).

EXAMPLE 2

Synthesis of H-Arg-Gly-Gln-(D)-Trp-Phe-Gly-Asp(OBu$^t$)2: Z-Phe-Gly-Asp(OBu$^t$)2

Z-Asp(OBu$^t$)$_2$ (920 mg) was dissolved in 150 ml of methanol and reduced with hydrogen in the presence of palladium black as the catalyst. The solvent was then distilled off. The residue was dissolved in 10 ml of DMF, and 864 mg of Z-Phe-Gly-OH and 873 mg of HONB were added. The mixture was ice-cooled and then stirred. With ice-cooling, 750 mg of DCC was added, and the mixture was stirred under the same conditions for 4 hours and then at room temperature for 12 hours. The precipitate was filtered off and the solvent was distilled off from the filtrate. The residue was dissolved in 200 ml of ethyl acetate, washed with 5%-NaHCO$_3$/water, 0.2N hydrochloric acid and water in that order, and dried over anhydrous sodium sulfate. The solvent was then distilled off. The residue was crystallized from a mixture of ether and petroleum benzin and the crystals were collected by filtration.

Yield 1.1 g (77.7%), m.p. 115°–117° C.
[α]$_D^{25}$ −23.8° (c=0.33, DMF).
Elemental analysis: Calcd. for C$_{31}$H$_{41}$O$_8$N$_3$: C 63.79; H 7.08; N 7.20, Found: C 63.55; H 7.20; N 7.19.

Z-(D)-Trp-Phe-Gly-Asp(OBu$^t$)2

In methanol, 500 mg of Z-Phe-Gly-Asp(OBu$^t$)$_2$ was reduced with hydrogen gas in the presence of palladium black as catalyst. The solvent was then distilled off. The residue was dissolved in 30 ml of acetonitrile, and Z-(D)-Trp-ONB (synthesized from 290 mg of Z-(D)-Trp-OH, 185 mg of HONB and 194 mg of DCC) was added with ice-cooling. The mixture was stirred at room temperature for 16 hours. The solvent was then distilled off. The residue was dissolved in 100 ml of ethyl acetate, washed with 5% NaHCO$_3$/water, 0.2N hydrochloric acid and water in that order and dried over anhydrous sodium sulfate. The solvent was distilled off and the resulting crystalline precipitate was collected from ether-petroleum benzin (2:1) to give 420 mg (63.7%) of the above-identified compound.

m.p. 134°–136° C.
[α]$_D^{26}$ −2.4° (c=0.29, DMF)
Elemental analysis: Calcd. for C$_{42}$H$_{51}$O$_9$N$_5$: C 65.52; H 6.68; N 9.10, Found: C 65.30; H 6.51; N 9.00.

Z-Gln-(D)-Trp-Phe-Gly-Asp(OBu$^t$)2

In methanol, 308 mg of Z-(D)-Trp-Phe-Gly-Asp(OBu$^t$)$_2$ was reduced with hydrogen gas in the presence of palladium black as catalyst. The solvent was then distilled off. The residue, 123 mg of Z-Gln-OH and 119 mg of HONB were dissolved in 20 ml of DMF and the solution was ice-cooled. With ice-cooling, 100 mg of DCC was added and the mixture was stirred. After about 4 hours, the temperature was returned to room temperature and the mixture was further stirred for about 12 hours. The insoluble matter was filtered off and the solvent was distilled off. To the residue was added acetonitrile to give a gel-form precipitate, which was collected by filtration and washed with acetonitrile-ether to give 250 mg (67.6%) of the above-identified compound.

m.p. 192°–194° C. (decompn.)
$[\alpha]_D^{26} - 7.0°$ (c=0.36, DMF)
Elemental analysis: Calcd. for $C_{47}H_{59}O_{11}N_7$: C 62.86; H 6.62; N 10.92, Found: C 62.51; H 6.41; N 10.98.

Z-Arg(NO$_2$)-Gly-Gln-(D)-Trp-Phe-Gly-Asp(OBu$^t$)2

Z-Gln-[D]-Trp-Phe-Gly-Asp(OBu$^t$)2 (130 mg) was dissolved in 50 ml of DMF and reduced with hydrogen gas in the presence of palladium black as catalyst. The solvent was concentrated to about one-third of its original volume. Z-Arg(NO$_2$)-Gly-OH (63 mg) and 63 mg of HOBt were added and the resulting solution was ice-cooled. With ice-cooling 48 mg of DCC was added, and the mixture was stirred at 0° C. for 5 hours and at room temperature for 20 hours. The insoluble matter was filtered off and the solvent was distilled off. To the residue was added ethyl acetate to give a gel-form precipitate, which was collected by filtration and washed with ethyl acetate and ether to give 150 mg (90.4%) of the above-identified compound.

m.p. 138°–140° C. (decompn.)
$[\alpha]_D^{26} - 6.0°$ (c=0.43, DMF)
Elemental analysis: Calcd. for $C_{55}H_{73}O_{15}N_{13}$: C 57.13; H 6.36; N 15.75, Found: C 57.21; H 6.50; N 15.92.

Synthesis of
H-Arg-Gly-Gln-(D)-Trp-Phe-Gly-Asp(OBu$^t$)2

Z-Arg(NO$_2$)-Gly-Gln-(D)-Trp-Phe-Gly-Asp(OBu$^t$)2 (129 mg) was dissolved in 50 ml of acetic acid and reduced with hydrogen gas in the presence of palladium black as catalyst. The solvent was then distilled off and water was a added to the residue. The insoluble matter was filtered off and lyophilized to give about 100 mg of a crude product, which was chromatographed on a Sephadex LH-20 column (2×85 cm) packed with 5N acetic acid. The fractions from 143 to 167 ml were combined and lyophilized to give 50 mg (45.7%) of the above-identified compound as a white powder.

$[\alpha]_D^{25} - 2.6°$ (c=0.27, 3N acetic acid)
Amino acid analysis: Arg 0.94(1), Trp 1.10(1), Asp 1.01(1), Glu 1.01(1), Gly 2.0(2), Phe 1.02(1), (Average recovery 88.8%).

EXAMPLE 3

Synthesis of H-Arg-Gly-Gln-Phe-Phe-Gly-Glu(OBu$^t$)2

Following the procedure of Example 1 but starting from Z-Glu(OBu$^t$)2, there was obtained a protected peptide Z-Arg(NO$_2$)-Gly-Gln-Phe-Phe-Gly-Glu-(OBu$^t$)2. This protected peptide was then subjected to Z elimination reaction followed by purification in the same manner as Examples 1 and 2 to give the above-identified compound.

$[\alpha]_D^{25} - 19.7°$ (c=0.15, 3N-acetic acid)
Amino acid analysis: Arg 0.94(1), Glu 2.28(2), Gly 2.0(2), Phe 1.99(2), (Average recovery: 68.4%)

EXAMPLE 4

Synthesis of
H-Arg-Pro-Thr-Gln-Phe-Phe-Gly-Asp(OBu$^t$)2

Following the procedure of Example 1, Z-Gln-Phe-Phe-Gly-Asp(OBu$^t$)2 was subjected to the reaction for elimination of Z, followed by repeated condensation (by the HONB-DCC method) and Z elimination reactions with Z-Thr-OH, Z-Pro-OH and Z-Arg(NO$_2$)-OH in that order, to give the desired protected peptide Z-Arg(NO$_2$)-Pro-Thr-Gln-Phe-Phe-Gly-Asp(OBu$^t$)2.

m.p. 118°–123° C.
$[\alpha]_D^{25} - 26.2°$ (c=0.22, DMF)
This protected peptide was then subjected to Z elimination reaction followed by purification by chromatography in the same manner as Examples 1–3 to give the above-identified compound.

$[\alpha]_D^{25} - 44.2°$ (c=1.12, 3N acetic acid).
Amino acid analysis: Arg 0.93(1), Asp 1.04(1), Thr 0.99(1), Glu 1.09(1), Pro 1.0(1), Gly 1.06(1), Phe 1.89(2), (Average recovery: 71.1%)

EXAMPLE 5

Synthesis of
H-Arg-Gly-Gln-Phe-Phe-(D)-Ala-Asp(OBu$^t$)2:
Z-(D)-Ala-Asp(OBu$^t$)2

In 100 ml of DMF were dissolved 2.2 g of Z-(D)-Ala-OH, 2.8 g of HCl-H-Asp(OBu$^t$)2, 1.5 ml of triethylamine and 2.2 g of HONB, and 2.3 g of DCC was added thereto with ice-cooling. The mixture was stirred for 4 hours and further stirred at room temperature for 10 hours. The precipitate was filtered off and the solvent of the filtrate was distilled off. The residue was dissolved in 300 ml of ethyl acetate. The solution was washed with 5% NaHCO$_3$/water, 0.2N hydrochloric acid and water in that order and dried over anhydrous sodium sulfate. The solvent was then distilled off. The resulting crystalline precipitate was recovered by filtration using 5% acetonitrile/ether, washed with ether and dried.

Yield 3.5 g (77.8%), m.p. 130° C.
$[\alpha]_D^{26} + 9.7°$ (c=0.19, methanol).
Elemental analysis: Calcd. for $C_{23}H_{24}O_7N_2$: C 61.31; H 7.61; N 6.22, Found: C 61.30; H 7.50; N 6.21.

Z-Phe-(D)-Ala-Asp(OBu$^t$)2

Z-(D)-Ala-Asp(OBu$^t$)2 (3 g) was dissolved in 300 ml of methanol and reduced with hydrogen in the presence of palladium black as catalyst. The solvent was distilled off and the residue was dissolved in 100 ml of DMF. To the solution were added 2.2 g of Z-Phe-OH and 1.6 g of HONB, and the mixture was ice-cooled followed by addition of 1.66 g of DCC. The resulting mixture was stirred at 0° C. for 4 hours and at room temperature for 8 hours. The precipitate was filtered off and the solvent of the filtrate was distilled off. The residue was extracted with 300 ml of ethyl acetate and the extract was washed with 5% NaHCO$_3$/water, 0.2N hydrochloric acid and water in that order and dried over anhydrous sodium sulfate. The solvent was then distilled off. To the crystalline precipitate was added petroleum benzin and the crystals were collected by filtration.

Yield 3.3 g (82.9%), m.p. 85°–87° C.
$[\alpha]_D^{26} + 11.9°$ (c=0.21, methanol).
Elemental analysis: Calcd. for $C_{32}H_{43}O_8N_3$: C 64.30; H 7.25; N 7.03, Found: C 64.43; H 7.29; N 7.22.

Z-Phe-Phe-(D)-Ala-Asp(OBu$^t$)2

Z-Phe-(D)-Ala-Asp(OBu$^t$)2 (1.6 g) was dissolved in 200 ml of methanol and reduced with hydrogen gas in the presence of palladium black as catalyst. The solvent was distilled off and the residue was dissolved in 100 ml of DMF. To the solution were added 881 mg of Z-Phe-OH and 636 mg of HONB, and the mixture was ice-cooled followed by addition of 668 mg of DCC. The resulting mixture was stirred at 0° C. for 4 hours and at room temperature for 12 hours. The insoluble matter was filtered off and the solvent of the filtrate was distilled off. To the residue was added 10 ml of acetonitrile and the solid was recovered by filtration.

Yield 960 mg (48.2%), m.p. 135°–138° C.
$[\alpha]_D^{26}$ −22.6° (c=0.35, DMF)
Elemental analysis: Calcd. for $C_{41}H_{52}O_9N_4$: C 66.11; H 7.04; N 7.52, Found: C 65.98; H 7.05; N 7.70.

Z-Gln-Phe-Phe-(D)-Ala-Asp(OBu$^t$)2

Z-Phe-Phe-(D)-Ala-Asp(OBu$^t$)$_2$ (500 mg) was dissolved in 150 ml of methanol and reduced with hydrogen in the presence of palladium black as catalyst. The solvent was then distilled off. The residue, 207 mg of Z-Gln-OH and 159 mg of HONB were dissolved in 50 ml of DMF and the solution was ice-cooled. With cooling, 168 mg of DCC was added, and the mixture was stirred at 0° C. for 6 hours and at room temperature for 12 hours. The insoluble matter was filtered off and the solvent of the filtrate was distilled off. To the residue was added 10 ml of acetonitrile and the solid was recovered by filtration.

Yield 735 mg (84.2%), m.p. 218°–222° C. (decompn.).
$[\alpha]_D^{26}$ −28.1° (c=0.32, DMF).
Elemental analysis: Calcd. for $C_{46}H_{60}O_{11}N_6$: C 63.28; H 6.93; N 9.63, Found: C 63.05; H 6.70; N 9.52.

H-Arg-Gly-Gln-Phe-Phe-(D)-Ala-Asp(OBu$^t$)2

Z-Gln-Phe-Phe-(D)-Ala-Asp(OBu$^t$)$_2$ (500 mg) was dissolved in 200 ml of methanol and reduced with hydrogen gas in the presence of palladium black as catalyst. The solvent was then distilled off. The residue, together with 235 mg of Z-Arg(NO$_2$)-Gly-OH and 155 mg of HOBt, was dissolved in 30 ml of DMF and the solution was ice-cooled. With cooling, 177 mg of DCC was added, and the mixture was stirred at 0° C. for 6 hours and at room temperature for 18 hours. The precipitate was filtered off and the filtrate was distilled under reduced pressure. To the residue was added ether containing 5% of acetonitrile and the solid was recovered by filtration. In the same manner as Examples 1–4, this product was further subjected to Z elimination reaction followed by purification by column chromatography to give the title compound.

Yield 110 mg (20.5%).
$[\alpha]_D^{25}$ −3.5° (c=0.2, 3N acetic acid)
Amino acid analysis: Arg 0.96(1), Asp 1.03(1), Glu 1.07(1), Gly 1.0(1), Ala 1.01(1), Phe 1.89(2), (Average recovery 70.5%).

EXAMPLE 6

Synthesis of
H-Arg-Gly-Gln-Phe-Phe-(D)-Trp-Asp(OBu$^t$)2:
Z-(D)-Trp-Asp(OBu$^t$)2

A mixture of 3.38 g of Z-(D)-Trp-OH and 2.8 g of HCl-H-Asp(OBu$^t$)$_2$ was treated and worked up in the same manner as the synthesis of Z-(D)-Ala-Asp(OBu$^t$)$_2$ in Example 5 to give 4.1 g (72.6%) of the desired product as an oil.

The thus-obtained Z-(D)-Trp-Asp(OBu$^t$)$_2$ was then subjected to repeated condensation reaction with Z-Phe-OH, Z-Phe-OH, Z-Gln-OH and Z-Arg(NO$_2$)-Gly-OH in that order to give a protected peptide. This protected peptide was further subjected to Z elimination reaction followed by purification by chromatography in the same manner as Examples 1–5 to give the above-identified compound.

Amino acid analysis: Arg 0.97(1), Trp 1.05(1), Asp 1.06(1), Glu 1.06(1), Gly 1.0(1), Phe 1.90(2), (Average recovery 74.5%)

EXAMPLE 7

Synthesis of H-Lys-Gly-Gln-Phe-Phe-Gly-Asp(OBu$^t$)2:
Z-Lys(Z)-Gly-OH

In 200 ml of dioxane-ethyl acetate (1:1) were dissolved 4.14 g of Z-Lys(Z)-OH and 2.16 g of HONB and the solution was ice-cooled. With cooling, 2.27 g of DCC was added, and the mixture was stirred at 0° C. for 2 hours and at room temperature for 3 hours. The precipitate was filtered off and the filtrate was distilled under reduced pressure. The residue was dissolved in 100 ml of DMF. In 50 ml of water were dissolved 1 g of H-Gly-OH and 0.9 g of NaHCO$_3$ and the solution was ice-cooled. To this solution was added the above-obtained DMF solution and the mixture was stirred vigorously. After 16 hours, the solvent was distilled off. The residue was dissolved in 150 ml of water and the solution was extracted with ether. The aqueous layer was adjusted to pH 2 with 1N hydrochloric acid and extracted with 300 ml of ethyl acetate. The ethyl acetate layer was washed with water and dried over anhydrous sodium sulfate. The solvent was then distilled off. To the crystalline precipitate was added ether and the crystals were collected by filtration.

Yield 400 mg (85.0%). m.p. 145°–147° C.
$[\alpha]_D^{26}$ −11.1° (c=0.44, methanol)
Elemental analysis: Calcd. for $C_{24}H_{29}O_7N_3$: C 61.13; H 6.20; N 8.91, Found: C 60.99; H 6.21; N 8.90.

Z-Gln-Phe-Phe-Gly-Asp(OBu$^t$)$_2$ and Lys(Z)-Gly-OH was subjected to condensation reaction, Z elimination reaction and purification by chromatography in the same manner as Example 1 to give 30 mg of the title compound.

Amino acid analysis: Lys 0.98(1), Asp 1.03(1), Glu 1.05(1), Gly 2.0(2), Phe 1.92(2), (Average recovery 65.2%).

EXAMPLE 8

Synthesis of
H-(D)-Arg-Gly-Gln-(D)-Trp-Phe-(D)-Trp-Asp(OBu$^t$)2: Z-Phe-(D)-Trp-Asp(OBu$^t$)2

In methanol, 4.1 g of Z-(D)-Trp-Asp(OBu$^t$)$_2$ was reduced with hydrogen gas in the presence of palladium black as catalyst. The solvent was then distilled off. The residue, together with 2.4 g of Z-Phe-OH and 1.7 g of HONB, was dissolved in 200 ml of DMF and the solution was ice-cooled. With cooling, 1.81 g of DCC was added, and the mixture was stirred at 0° C. for 6 hours and at room temperature for 8 hours. The insoluble matter was filtered off and the filtrate was distilled under reduced pressure. To the residue was added acetonitrile and the crystals were collected by filtration.

Yield 3.9 g (75.4%), m.p. 157°–158° C.
$[\alpha]_D^{26}$ +13.6° (c=0.46, methanol).
Elemental analysis Calcd. for $C_{40}H_{48}O_8N_4$: C 67.39; H 6.79; N 7.86, Found: C 67.21; H, 6.91; N 7.80.

Z-(D)-Arg(NO$_2$)-Gly-OH

In the same manner as the synthesis of Z-Arg(NO$_2$)-Gly-OH in Example 1, Z-(D)-Arg(NO$_2$)-Gly-OEt was synthesized from Z-(D)-Arg(NO$_2$)-OH. The subsequent saponification of the ester gave the above-identified compound.

m.p. 121° C. (decompn.)

[α]$_D^{25}$+8.7° (c=0.8, methanol)

Elemental analysis: Calcd. for $C_{16}H_{22}O_7N_6$: C 46.83; H 5.40; N 20.48, Found: C 46.72; H 5.56; N 20.50.

Z-Phe-(D)-Trp-Asp(OBu$^t$)2 was subjected to the reactions of Example 2 and finally reacted with Z-(D)-Arg(NO$_2$)-Gly-OH, instead of Z-Arg(NO$_2$)-Gly-OH, to give a protected peptide. This protected peptide was subjected to Z elimination reaction followed by purification by chromatography in the same manner as Examples 1–7 to give 20 mg of the desired product.

Amino acid analysis: Arg 0.99(1), Trp 1.89(2), Asp 1.03(1), Glu 1.05(1), Gly 1.0(1), Phe 0.96(1), (Average recovery: 72.0%).

EXAMPLE 9

Synthesis of H-Arg-Gln-Phe-Phe-Gly-Asp(OBu$^t$)2

In 100 ml of DMF was dissolved 200 mg of Z-Gln-Phe-Phe-Gly-Asp(OBu$^t$)2 and catalytic reduction was carried out using palladium black as catalyst. The reaction mixture was concentrated to one-third its original volume and 100 mg of Z-Arg(NO$_2$)-OH and 57 mg of HOBt were added. The mixture was ice-cooled and 69 mg of DCC was added. The mixture was stirred at 0° C. for 8 hours and at room temperature for 20 hours. The insoluble matter was filtered off and the solvent was distilled off. To the residue was added ethyl acetate, and the resulting precipitate was collected by filtration, dried and dissolved in 100 ml of acetic acid. Catalytic reduction was carried out in a hydrogen gas stream using palladium black as catalyst. The reduction product was lyophilized, dissolved in 0.5 ml of 5N acetic acid and then chromatographed on a Sephadex LH-20 column packed with the same solvent. The fractions from 104 to 123 ml were combined and lyophilized to give the above-identified compound.

Yield 128 mg (62.3%),

[α]$_D^{25}$−10.4° (c=0.24, 3N acetic acid).

Amino acid analysis: Arg 1.0(1), Asp 1.02(1), Glu 1.06(1), Gly 1.0(1), Phe 1.89(2), (Average recovery: 70.4%)

EXAMPLE 10

Synthesis of H-Lys-Gln-Phe-Phe-Gly-Asp(OBu$^t$)2

Following the procedure of Example 9 but using 200 mg of Z-Gln-Phe-Phe-Gly-Asp(OBu$^t$)2 and 104 mg of Z-Lys(Z)-OH, a protected peptide was obtained. This protected peptide was subjected to Z elimination reaction followed by purification by chromatography in the same manner as Example 9 to give the above-identified compound.

Yield 83 mg (42.0%).

Amino acid analysis: Lys 0.97(1), Asp 1.02(1), Glu 1.06(1), Gly 1.0(1), Phe 2.04(2), (Average recovery 67.4%).

EXAMPLE 11

Production of H-Arg-Gly-Gln-Phe-Phe-Gly-Asp(OBu$^t$)2.2HCl

In 2 ml of water was dissolved 10 mg of the compound obtained by Example 1 together with 2 ml of 0.01N-HCl. The solution was stirred for 15 minutes, and then lyophilized to give the above-identified compound as a powder. Yield 9 mg (89%).

EXAMPLE 12

Production of H-Arg-Gly-Gln-(D)-Trp-Phe-Gly-Asp(OBu$^t$)2.H$_2$SO$_4$

In 3 ml of water was dissolved 20 mg of the compound obtained by Example 2 together with 1.8 ml of 0.01N H$_2$SO$_4$, and stirred for 15 minutes. The solution was liophilized to give the above-identified compound as a powder.

Yield 19 mg (97%).

EXAMPLE 13

Production of H-(D)-Arg-Gly-Gln-(D)-Trp-Phe-(D)-Trp-Asp(OBu$^t$)2.citrate

In 3 ml of water was dissolved 12 mg of the compound obtained by Example 8 together with 1.4 mg of citric acid monohydrate. The solution was lyophilized, and the obtained powder was dissolved in 2 ml of water. Lyophilization was conducted again to give the above-identified compound. Yield 10 mg (83%).

EXAMPLE 14

Production of H-Lys-Gly-Gln-Phe-Phe-Gly-Asp(OBu$^t$)2.tartarate

In 2 ml of water was dissolved 10 mg of the compound obtained by Example 7 together with 1.5 mg of tartaric acid. The lyophilization was repeated three times to give the above-identified compound.

Yield 10 mg (97%).

EXAMPLE 15

In 1 l of physiological saline was dissolved 3.0 g of the H-(D)-Arg-Gly-Gln-(D)Trp-Phe-(D)-Trp-Asp(OBu$^t$)2 obtained in Example 8 and the solution was filtered through a microfilter and distributed into ampoules at the rate of 2.2 ml per ampoule. After sealing, the ampoules were sterilized at 110° C. for 30 minutes. The above procedure gives the ampoule of H-(D)Arg-Gly-Gln-(D)Trp-Phe-(D)Trp-Asp(OBu$^t$)2 for subcutaneous, intravenous or intramuscular administration.

EXAMPLE 16

In 1 l of distilled water was dissolved 30 g of the H-Arg-Gly-Gln-(D)Trp-Phe-Gly-Asp(OBu$^t$)2 obtained in Example 2 and, then, 10 g of mannitol was added and dissolved. The solution was sterilized through a microfilter and distributed into ampoules at the rate of 2 ml per ampoule. The ampoules were dried in a freeze-dryer and sealed. The above procedure provides ampoules for extemporaneous administration. To use the ampoule, it is unsealed and dissolved for example in 2 ml of physiological saline to give an injectable solution for subcutaneous, intravenous or intramuscular administration.

What we claim is:

1. A compound of the formula:

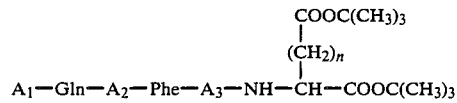

wherein

A$_1$ is arginine or lysine or a di- or tripeptide residue having arginine or lysine at its N-terminal and wherein the additional amino acid residue constituting the di- or tripeptide are Gly, Pro, (D)-Pro, Thr, (D)-Thr, Ser, (D)-Ser, Ala, (D)-Ala, Val, (D)-Val, Leu, (D)-Leu, Ile, (D)-Ile, Gln, (D)-Gln, Asn or (D)-Asn;

$A_2$ is an aromatic amino acid residue of the class consisting of Trp, (D)-Trp, Phe (D)-Phe, Tyr or (D)-Tyr;

$A_3$ is a neutral amino acid residue of the class consisting of Gly, Ala, (D)-Ala, Val, (D)-Val, Leu, (D)-Leu, Ile or (D)-Ile or aromatic amino acid residue of the class consisting of Trp, (D)-Trp, Tyr, (D)-Tyr, Phe or (D)-Phe; and, n is 0, 1 or 2, or a pharmaceutically acceptable salt thereof.

2. A compound according to claim 1 wherein $A_1$ is a di-peptide residue.

3. A compound according to claim 1 wherein $A_1$ is a tripeptide residue.

4. The compound according to claim 1, wherein $A_1$ is Arg-Gly, $A_2$ is Phe, $A_3$ is Gly and n is 1.

5. The compound according to claim 1, wherein $A_1$ is Arg-Gly, $A_2$ is (D)-Trp, $A_3$ is Gly and n is 1.

6. The compound according to claim 1, wherein $A_1$ is Arg-Gly, $A_2$ is Phe, $A_3$ is Gly and n is 2.

7. The compound according to claim 1, wherein $A_1$ is Arg-Pro-Thr, $A_2$ is Phe, $A_3$ is Gly and n is 1.

8. The compound according to claim 1, wherein $A_1$ is Arg-Gly, $A_2$ is Phe, $A_3$ is (D)-Ala and n is 1.

9. The compound according to claim 1, wherein $A_1$ is Arg-Gly, $A_2$ is Phe, $A_3$ is (D)-Trp and n is 1.

10. The compound according to claim 1, wherein $A_1$ is Lys-Gly, $A_2$ is Phe, $A_3$ is Gly and n is 1.

11. The compound according to claim 1, wherein $A_1$ is (D)-Arg-Gly, $A_2$ is (D)-Trp, $A_3$ is (D)-Trp and n is 1.

12. The compound according to claim 1, wherein $A_1$ is Arg, $A_2$ is Phe, $A_3$ is Gly and n is 1.

13. The compound according to claim 1, wherein $A_1$ is Lys, $A_2$ is Phe, $A_3$ Gly and n is 1.

14. A pharmaceutical composition for pain-relieving in mammalian animals, which contains an effective amount of a compound of the formula:

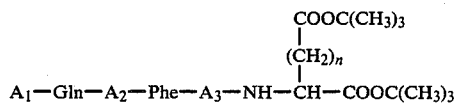

wherein $A_1$ is arginine or lysine or a di- or tri-peptide residue having arginine or lysine at its N-terminal and wherein the additional amino acid residues constituting the di- or tripeptide are Gly, Pro, (D)-Pro, Thr, (D)-Thr, Ser, (D)-Ser, Ala, (D)-Ala, Val, (D)-Val, Leu, (D)-Leu, Ile, (D)-Ile, Gln, (D)-Gln, Asn or (D)-Asn;

$A_2$ is an aromatic amino acid residue of the class consisting of Trp, (D)-Trp, Phe (D)-Phe, Tyr or (D)-Tyr;

$A_3$ is a neutral amino acid residue of the class consisting of Gly, Ala, (D)-Ala, Val, (D)-Val, Leu, (D)-Leu, Ile or (D)-Ile or aromatic amino acid residue of the class consisting of Trp, (D)-Trp, Tyr, (D)-Tyr, Phe or (D)-Phe;

n is 0, 1 or 2, and a pharmacologically acceptable carrier.

* * * * *